US012008494B2

United States Patent
Delellis et al.

(10) Patent No.: US 12,008,494 B2
(45) Date of Patent: Jun. 11, 2024

(54) TECHNIQUES FOR BEHAVIORAL PAIRING IN A MULTISTAGE TASK ASSIGNMENT SYSTEM

(71) Applicant: Afiniti, Ltd., Hamilton (BM)

(72) Inventors: David J. Delellis, Doylestown, PA (US); Randal E. Holl, Annapolis, MD (US)

(73) Assignee: AFINITI, LTD., Hamilton (BM)

(*) Notice: Subject to any disclaimer, the term of this patent is extended or adjusted under 35 U.S.C. 154(b) by 150 days.

(21) Appl. No.: 17/097,559

(22) Filed: Nov. 13, 2020

(65) Prior Publication Data

US 2021/0065095 A1   Mar. 4, 2021

Related U.S. Application Data

(63) Continuation of application No. 16/209,295, filed on Dec. 4, 2018, now Pat. No. 10,867,263.

(51) Int. Cl.
| | |
|---|---|
| *G06Q 10/06* | (2023.01) |
| *G06Q 10/0631* | (2023.01) |
| *G16H 20/10* | (2018.01) |
| *H04M 3/51* | (2006.01) |
| *H04M 3/523* | (2006.01) |

(52) U.S. Cl.
CPC ..... *G06Q 10/063112* (2013.01); *G16H 20/10* (2018.01); *H04M 3/5175* (2013.01); *H04M 3/5233* (2013.01)

(58) Field of Classification Search
CPC .................................................... G06Q 10/06
See application file for complete search history.

(56) References Cited

U.S. PATENT DOCUMENTS

| | | | |
|---|---|---|---|
| 5,155,763 A | 10/1992 | Bigus et al. | |
| 5,206,903 A | 4/1993 | Kohler et al. | |

(Continued)

FOREIGN PATENT DOCUMENTS

| | | |
|---|---|---|
| AU | 2008349500 C1 | 5/2014 |
| AU | 2009209317 B2 | 5/2014 |

(Continued)

OTHER PUBLICATIONS

Yongho Kim and Eric T Matson, A Realistic Decision Making for Task Allocation in Heterogeneous Multi-agent Systems, M2M lab, Computer and Information Technology, Purdue University, 2016. (Year: 2016).*

(Continued)

*Primary Examiner* — Kurtis Gills
(74) *Attorney, Agent, or Firm* — Rothwell, Figg, Ernst & Manbeck, P.C.

(57) ABSTRACT

Techniques for behavioral pairing in a multistage task assignment system are disclosed. In one particular embodiment, the techniques may be realized as a method for behavioral pairing in a multistage task assignment system comprising: determining, by at least one computer processor communicatively coupled to and configured to operate in the multistage task assignment system, one or more characteristics of a task; determining, by the at least one computer processor and based at least on the one or more characteristics of the task, a sequence of agents; and pairing, by the at least one computer processor, the task with the sequence of agents.

14 Claims, 6 Drawing Sheets

(56) References Cited

U.S. PATENT DOCUMENTS

| | | |
|---|---|---|
| 5,327,490 A | 7/1994 | Cave |
| 5,537,470 A | 7/1996 | Lee |
| 5,702,253 A | 12/1997 | Bryce et al. |
| 5,825,869 A | 10/1998 | Brooks et al. |
| 5,903,641 A | 5/1999 | Tonisson |
| 5,907,601 A | 5/1999 | David et al. |
| 5,926,538 A | 7/1999 | Deryugin et al. |
| 6,021,428 A | 2/2000 | Miloslavsky |
| 6,044,355 A | 3/2000 | Crockett et al. |
| 6,044,468 A | 3/2000 | Osmond |
| 6,049,603 A | 4/2000 | Schwartz et al. |
| 6,052,460 A | 4/2000 | Fisher et al. |
| 6,064,731 A | 5/2000 | Flockhart et al. |
| 6,088,444 A | 7/2000 | Walker et al. |
| 6,163,607 A | 12/2000 | Bogart et al. |
| 6,222,919 B1 | 4/2001 | Hollatz et al. |
| 6,292,555 B1 | 9/2001 | Okamoto |
| 6,324,282 B1 | 11/2001 | McIllwaine et al. |
| 6,333,979 B1 | 12/2001 | Bondi et al. |
| 6,389,132 B1 | 5/2002 | Price |
| 6,389,400 B1 | 5/2002 | Bushey et al. |
| 6,408,066 B1 | 6/2002 | Andruska et al. |
| 6,411,687 B1 | 6/2002 | Bohacek et al. |
| 6,424,709 B1 | 7/2002 | Doyle et al. |
| 6,434,230 B1 | 8/2002 | Gabriel |
| 6,496,580 B1 | 12/2002 | Chack |
| 6,504,920 B1 | 1/2003 | Okon et al. |
| 6,519,335 B1 | 2/2003 | Bushnell |
| 6,519,568 B1 | 2/2003 | Harvey et al. |
| 6,526,135 B1 | 2/2003 | Paxson |
| 6,535,600 B1 | 3/2003 | Fisher et al. |
| 6,535,601 B1 | 3/2003 | Flockhart et al. |
| 6,570,980 B1 | 5/2003 | Baruch |
| 6,587,556 B1 | 7/2003 | Judkins et al. |
| 6,603,854 B1 | 8/2003 | Judkins et al. |
| 6,639,976 B1 | 10/2003 | Shellum et al. |
| 6,661,889 B1 | 12/2003 | Flockhart et al. |
| 6,704,410 B1 | 3/2004 | McFarlane et al. |
| 6,707,904 B1 | 3/2004 | Judkins et al. |
| 6,714,643 B1 | 3/2004 | Gargeya et al. |
| 6,744,878 B1 | 6/2004 | Komissarchik et al. |
| 6,763,104 B1 | 7/2004 | Judkins et al. |
| 6,774,932 B1 | 8/2004 | Ewing et al. |
| 6,775,378 B1 | 8/2004 | Villena et al. |
| 6,798,876 B1 | 9/2004 | Bala |
| 6,829,348 B1 | 12/2004 | Schroeder et al. |
| 6,832,203 B1 | 12/2004 | Villena et al. |
| 6,859,529 B2 | 2/2005 | Duncan et al. |
| 6,895,083 B1 | 5/2005 | Bers et al. |
| 6,922,466 B1 | 7/2005 | Peterson et al. |
| 6,937,715 B2 | 8/2005 | Delaney |
| 6,956,941 B1 | 10/2005 | Duncan et al. |
| 6,970,821 B1 | 11/2005 | Shambaugh et al. |
| 6,978,006 B1 | 12/2005 | Polcyn |
| 7,023,979 B1 | 4/2006 | Wu et al. |
| 7,039,166 B1 | 5/2006 | Peterson et al. |
| 7,050,566 B2 | 5/2006 | Becerra et al. |
| 7,050,567 B1 | 5/2006 | Jensen |
| 7,062,031 B2 | 6/2006 | Becerra et al. |
| 7,068,775 B1 | 6/2006 | Lee |
| 7,092,509 B1 | 8/2006 | Mears et al. |
| 7,103,172 B2 | 9/2006 | Brown et al. |
| 7,158,628 B2 | 1/2007 | McConnell et al. |
| 7,184,540 B2 | 2/2007 | Dezonno et al. |
| 7,209,549 B2 | 4/2007 | Reynolds et al. |
| 7,231,032 B2 | 6/2007 | Nevman et al. |
| 7,231,034 B1 | 6/2007 | Rikhy et al. |
| 7,236,584 B2 | 6/2007 | Torba |
| 7,245,716 B2 | 7/2007 | Brown et al. |
| 7,245,719 B2 | 7/2007 | Kawada et al. |
| 7,266,251 B2 | 9/2007 | Rowe |
| 7,269,253 B1 | 9/2007 | Wu et al. |
| 7,353,388 B1 | 4/2008 | Gilman et al. |
| 7,372,952 B1 | 5/2008 | Wu et al. |
| 7,398,224 B2 | 7/2008 | Cooper |
| 7,593,521 B2 | 9/2009 | Becerra et al. |
| 7,676,034 B1 | 3/2010 | Wu et al. |
| 7,725,339 B1 | 5/2010 | Aykin |
| 7,734,032 B1 | 6/2010 | Kiefhaber et al. |
| 7,798,876 B2 | 9/2010 | Mix |
| 7,826,597 B2 | 11/2010 | Berner et al. |
| 7,864,944 B2 | 1/2011 | Khouri et al. |
| 7,899,177 B1 | 3/2011 | Bruening et al. |
| 7,916,858 B1 | 3/2011 | Heller et al. |
| 7,940,917 B2 | 5/2011 | Lauridsen et al. |
| 7,961,866 B1 | 6/2011 | Boutcher et al. |
| 7,995,717 B2 | 8/2011 | Conway et al. |
| 8,000,989 B1 | 8/2011 | Kiefhaber et al. |
| 8,010,607 B2 | 8/2011 | McCormack et al. |
| 8,094,790 B2 | 1/2012 | Conway et al. |
| 8,126,133 B1 | 2/2012 | Everingham et al. |
| 8,140,441 B2 | 3/2012 | Cases et al. |
| 8,175,253 B2 | 5/2012 | Knott et al. |
| 8,229,102 B2 | 7/2012 | Knott et al. |
| 8,249,245 B2 | 8/2012 | Jay et al. |
| 8,295,471 B2 | 10/2012 | Spottiswoode et al. |
| 8,300,798 B1 | 10/2012 | Wu et al. |
| 8,306,212 B2 | 11/2012 | Arora |
| 8,359,219 B2 | 1/2013 | Chishti et al. |
| 8,433,597 B2 | 4/2013 | Chishti et al. |
| 8,472,611 B2 | 6/2013 | Chishti |
| 8,565,410 B2 | 10/2013 | Chishti et al. |
| 8,634,542 B2 | 1/2014 | Spottiswoode et al. |
| 8,644,490 B2 | 2/2014 | Stewart |
| 8,670,548 B2 | 3/2014 | Xie et al. |
| 8,699,694 B2 | 4/2014 | Chishti et al. |
| 8,712,821 B2 | 4/2014 | Spottiswoode |
| 8,718,271 B2 | 5/2014 | Spottiswoode |
| 8,724,797 B2 | 5/2014 | Chishti et al. |
| 8,731,178 B2 | 5/2014 | Chishti et al. |
| 8,737,595 B2 | 5/2014 | Chishti et al. |
| 8,750,488 B2 | 6/2014 | Spottiswoode et al. |
| 8,761,380 B2 | 6/2014 | Kohler et al. |
| 8,781,100 B2 | 7/2014 | Spottiswoode et al. |
| 8,781,106 B2 | 7/2014 | Afzal |
| 8,792,630 B2 | 7/2014 | Chishti et al. |
| 8,824,658 B2 | 9/2014 | Chishti |
| 8,831,207 B1 | 9/2014 | Agarwal |
| 8,856,869 B1 | 10/2014 | Brinskelle |
| 8,879,715 B2 | 11/2014 | Spottiswoode et al. |
| 8,903,079 B2 | 12/2014 | Xie et al. |
| 8,913,736 B2 | 12/2014 | Kohler et al. |
| 8,929,537 B2 | 1/2015 | Chishti et al. |
| 8,938,063 B1 | 1/2015 | Hackbarth et al. |
| 8,995,647 B2 | 3/2015 | Li et al. |
| 9,020,137 B2 | 4/2015 | Chishti et al. |
| 9,025,757 B2 | 5/2015 | Spottiswoode et al. |
| 9,215,323 B2 | 12/2015 | Chishti |
| 9,277,055 B2 | 3/2016 | Spottiswoode et al. |
| 9,300,802 B1 | 3/2016 | Chishti |
| 9,426,296 B2 | 8/2016 | Chishti et al. |
| 9,712,676 B1 | 7/2017 | Chishti |
| 9,712,679 B2 | 7/2017 | Chishti et al. |
| 9,781,269 B2 | 10/2017 | Chishti et al. |
| 9,787,841 B2 | 10/2017 | Chishti et al. |
| 9,930,180 B1 | 3/2018 | Kan et al. |
| 9,942,405 B1 | 4/2018 | Kan et al. |
| RE46,986 E | 8/2018 | Chishti et al. |
| 10,116,795 B1 | 10/2018 | Chishti et al. |
| 10,116,800 B1 | 10/2018 | Kan et al. |
| 10,135,987 B1 | 11/2018 | Chishti et al. |
| RE47,201 E | 1/2019 | Chishti et al. |
| 10,284,727 B2 | 5/2019 | Kan et al. |
| 10,404,861 B2 | 9/2019 | Kan et al. |
| 2001/0032120 A1 | 10/2001 | Stuart et al. |
| 2001/0044896 A1 | 11/2001 | Schwartz et al. |
| 2002/0018554 A1 | 2/2002 | Jensen et al. |
| 2002/0046030 A1 | 4/2002 | Haritsa et al. |
| 2002/0059164 A1 | 5/2002 | Shtivelman |
| 2002/0082736 A1 | 6/2002 | Lech et al. |
| 2002/0110234 A1 | 8/2002 | Walker et al. |
| 2002/0111172 A1 | 8/2002 | DeWolf et al. |
| 2002/0131399 A1 | 9/2002 | Philonenko |
| 2002/0138285 A1 | 9/2002 | DeCotiis et al. |

(56) References Cited

U.S. PATENT DOCUMENTS

| | | |
|---|---|---|
| 2002/0143599 A1 | 10/2002 | Nourbakhsh et al. |
| 2002/0161765 A1 | 10/2002 | Kundrot et al. |
| 2002/0184069 A1 | 12/2002 | Kosiba et al. |
| 2002/0196845 A1 | 12/2002 | Richards et al. |
| 2003/0002653 A1 | 1/2003 | Uckun |
| 2003/0059029 A1 | 3/2003 | Mengshoel et al. |
| 2003/0081757 A1 | 5/2003 | Mengshoel et al. |
| 2003/0095652 A1 | 5/2003 | Mengshoel et al. |
| 2003/0169870 A1 | 9/2003 | Stanford |
| 2003/0174830 A1 | 9/2003 | Boyer et al. |
| 2003/0217016 A1 | 11/2003 | Pericle |
| 2004/0028211 A1 | 2/2004 | Culp et al. |
| 2004/0057416 A1 | 3/2004 | McCormack |
| 2004/0096050 A1 | 5/2004 | Das et al. |
| 2004/0098274 A1 | 5/2004 | Dezonno et al. |
| 2004/0101127 A1 | 5/2004 | Dezonno et al. |
| 2004/0109555 A1 | 6/2004 | Williams |
| 2004/0133434 A1 | 7/2004 | Szlam et al. |
| 2004/0210475 A1 | 10/2004 | Starnes et al. |
| 2004/0230438 A1 | 11/2004 | Pasquale et al. |
| 2004/0267816 A1 | 12/2004 | Russek |
| 2005/0004825 A1 | 1/2005 | Ehrler et al. |
| 2005/0013428 A1 | 1/2005 | Walters |
| 2005/0043986 A1 | 2/2005 | McConnell et al. |
| 2005/0047581 A1 | 3/2005 | Shaffer et al. |
| 2005/0047582 A1 | 3/2005 | Shaffer et al. |
| 2005/0071223 A1 | 3/2005 | Jain et al. |
| 2005/0129212 A1 | 6/2005 | Parker |
| 2005/0135593 A1 | 6/2005 | Becerra et al. |
| 2005/0135596 A1 | 6/2005 | Zhao |
| 2005/0187802 A1 | 8/2005 | Koeppel |
| 2005/0195960 A1 | 9/2005 | Shaffer et al. |
| 2005/0286709 A1 | 12/2005 | Horton et al. |
| 2006/0098803 A1 | 5/2006 | Bushey et al. |
| 2006/0110052 A1 | 5/2006 | Finlayson |
| 2006/0124113 A1 | 6/2006 | Roberts |
| 2006/0184040 A1 | 8/2006 | Keller et al. |
| 2006/0222164 A1 | 10/2006 | Contractor et al. |
| 2006/0233326 A1 | 10/2006 | Erhart et al. |
| 2006/0233346 A1 | 10/2006 | McIlwaine et al. |
| 2006/0262918 A1 | 11/2006 | Karnalkar et al. |
| 2006/0262922 A1 | 11/2006 | Margulies et al. |
| 2007/0036323 A1 | 2/2007 | Travis |
| 2007/0071222 A1 | 3/2007 | Flockhart et al. |
| 2007/0116240 A1 | 5/2007 | Foley et al. |
| 2007/0121602 A1 | 5/2007 | Sin et al. |
| 2007/0121829 A1 | 5/2007 | Tal et al. |
| 2007/0136342 A1 | 6/2007 | Singhai et al. |
| 2007/0153996 A1 | 7/2007 | Hansen |
| 2007/0154007 A1 | 7/2007 | Bernhard |
| 2007/0174111 A1 | 7/2007 | Anderson et al. |
| 2007/0198322 A1 | 8/2007 | Bourne et al. |
| 2007/0211881 A1 | 9/2007 | Parker-Stephen |
| 2007/0219816 A1 | 9/2007 | Van Luchene et al. |
| 2007/0274502 A1 | 11/2007 | Brown |
| 2008/0002823 A1 | 1/2008 | Fama et al. |
| 2008/0008309 A1 | 1/2008 | Dezonno et al. |
| 2008/0046386 A1 | 2/2008 | Pieraccinii et al. |
| 2008/0065476 A1 | 3/2008 | Klein et al. |
| 2008/0109797 A1 | 5/2008 | Khetarpal et al. |
| 2008/0118052 A1 | 5/2008 | Houmaidi et al. |
| 2008/0144803 A1 | 6/2008 | Jaiswal et al. |
| 2008/0152122 A1 | 6/2008 | Idan et al. |
| 2008/0181389 A1 | 7/2008 | Bourne et al. |
| 2008/0199000 A1 | 8/2008 | Su et al. |
| 2008/0205611 A1 | 8/2008 | Jordan et al. |
| 2008/0267386 A1 | 10/2008 | Cooper |
| 2008/0273687 A1 | 11/2008 | Knott et al. |
| 2009/0043670 A1 | 2/2009 | Johansson et al. |
| 2009/0063238 A1 | 3/2009 | Storzum et al. |
| 2009/0086933 A1 | 4/2009 | Patel et al. |
| 2009/0190740 A1 | 7/2009 | Chishti et al. |
| 2009/0190743 A1 | 7/2009 | Spottiswoode |
| 2009/0190744 A1 | 7/2009 | Xie et al. |
| 2009/0190745 A1 | 7/2009 | Xie et al. |
| 2009/0190746 A1 | 7/2009 | Chishti et al. |
| 2009/0190747 A1 | 7/2009 | Spottiswoode |
| 2009/0190748 A1 | 7/2009 | Chishti et al. |
| 2009/0190749 A1 | 7/2009 | Xie et al. |
| 2009/0190750 A1 | 7/2009 | Xie et al. |
| 2009/0232294 A1 | 9/2009 | Xie et al. |
| 2009/0234710 A1 | 9/2009 | Belgaied Hassine et al. |
| 2009/0245493 A1 | 10/2009 | Chen et al. |
| 2009/0249083 A1 | 10/2009 | Forlenza et al. |
| 2009/0304172 A1 | 12/2009 | Becerra et al. |
| 2009/0305172 A1 | 12/2009 | Tanaka et al. |
| 2009/0318111 A1 | 12/2009 | Desai et al. |
| 2009/0323921 A1 | 12/2009 | Spottiswoode et al. |
| 2010/0020959 A1 | 1/2010 | Spottiswoode |
| 2010/0020961 A1 | 1/2010 | Spottiswoode |
| 2010/0054431 A1 | 3/2010 | Jaiswal et al. |
| 2010/0054452 A1 | 3/2010 | Afzal |
| 2010/0054453 A1 | 3/2010 | Stewart |
| 2010/0086120 A1 | 4/2010 | Brussat et al. |
| 2010/0111285 A1 | 5/2010 | Chishti |
| 2010/0111286 A1 | 5/2010 | Chishti |
| 2010/0111287 A1 | 5/2010 | Xie et al. |
| 2010/0111288 A1 | 5/2010 | Afzal et al. |
| 2010/0142698 A1 | 6/2010 | Spottiswoode et al. |
| 2010/0158238 A1 | 6/2010 | Saushkin |
| 2010/0183138 A1 | 7/2010 | Spottiswoode et al. |
| 2010/0303225 A1* | 12/2010 | Shashkov ............ H04M 3/5175 379/265.11 |
| 2011/0022357 A1 | 1/2011 | Vock et al. |
| 2011/0031112 A1 | 2/2011 | Birang et al. |
| 2011/0069821 A1 | 3/2011 | Korolev et al. |
| 2011/0125048 A1 | 5/2011 | Causevic et al. |
| 2011/0206199 A1 | 8/2011 | Arora |
| 2011/0288900 A1 | 11/2011 | McQueen et al. |
| 2012/0051536 A1 | 3/2012 | Chishti et al. |
| 2012/0051537 A1 | 3/2012 | Chishti et al. |
| 2012/0183131 A1 | 7/2012 | Kohler et al. |
| 2012/0224680 A1 | 9/2012 | Spottiswoode et al. |
| 2012/0278136 A1 | 11/2012 | Flockhart et al. |
| 2012/0291041 A1* | 11/2012 | Cipar ..................... G06F 9/5011 718/104 |
| 2013/0003959 A1 | 1/2013 | Nishikawa et al. |
| 2013/0022194 A1 | 1/2013 | Flockhart et al. |
| 2013/0051545 A1 | 2/2013 | Ross et al. |
| 2013/0251137 A1 | 9/2013 | Chishti et al. |
| 2013/0268941 A1* | 10/2013 | Cherkasova .......... G06F 9/5066 718/104 |
| 2013/0287202 A1 | 10/2013 | Flockhart et al. |
| 2014/0044246 A1 | 2/2014 | Klemm et al. |
| 2014/0079210 A1 | 3/2014 | Kohler et al. |
| 2014/0119531 A1 | 5/2014 | Tuchman et al. |
| 2014/0119533 A1 | 5/2014 | Spottiswoode et al. |
| 2014/0122143 A1* | 5/2014 | Fletcher ............. G06Q 10/0631 705/7.14 |
| 2014/0142998 A1* | 5/2014 | Kroeger ........... G06Q 10/06311 705/7.13 |
| 2014/0270133 A1 | 9/2014 | Conway et al. |
| 2014/0341370 A1 | 11/2014 | Li et al. |
| 2015/0055772 A1 | 2/2015 | Klemm et al. |
| 2015/0066529 A1* | 3/2015 | Lattuca .................. G16H 40/20 705/2 |
| 2015/0237208 A1 | 8/2015 | Chishti et al. |
| 2015/0281448 A1 | 10/2015 | Putra et al. |
| 2015/0294251 A1* | 10/2015 | Hildmann ........ G06Q 10/06311 705/7.13 |
| 2016/0080573 A1* | 3/2016 | Chishti ............... H04M 3/5183 379/265.11 |
| 2016/0086121 A1* | 3/2016 | Heilbrunn ........ G06Q 10/06393 705/7.39 |
| 2016/0266930 A1 | 9/2016 | Jones et al. |
| 2017/0013131 A1 | 1/2017 | Craib |
| 2017/0064080 A1 | 3/2017 | Chishti et al. |
| 2017/0064081 A1 | 3/2017 | Chishti et al. |
| 2017/0316438 A1 | 11/2017 | Konig et al. |
| 2017/0323211 A1* | 11/2017 | Bencke .................. G06Q 10/00 |
| 2018/0316793 A1 | 11/2018 | Kan et al. |

(56) References Cited

U.S. PATENT DOCUMENTS

| | | | |
|---|---|---|---|
| 2018/0316794 A1 | 11/2018 | Kan et al. | |
| 2019/0222697 A1 | 7/2019 | Kan et al. | |
| 2019/0301143 A1* | 10/2019 | Miller | B60K 37/06 |

FOREIGN PATENT DOCUMENTS

| | | | |
|---|---|---|---|
| AU | 2009311534 B2 | 8/2014 | |
| CN | 102301688 B | 5/2014 | |
| CN | 102017591 B | 11/2014 | |
| EP | 0493292 A2 | 7/1992 | |
| EP | 0949793 A1 | 10/1999 | |
| EP | 1032188 A1 | 8/2000 | |
| EP | 1335572 A2 | 8/2003 | |
| JP | 11-098252 A | 4/1999 | |
| JP | 2000-069168 A | 3/2000 | |
| JP | 2000-078291 A | 3/2000 | |
| JP | 2000-078292 A | 3/2000 | |
| JP | 2000-092213 A | 3/2000 | |
| JP | 2000-507420 A | 6/2000 | |
| JP | 2000-236393 A | 8/2000 | |
| JP | 2000-253154 A | 9/2000 | |
| JP | 2001-292236 A | 10/2001 | |
| JP | 2001-518753 A | 10/2001 | |
| JP | 2002-297900 A | 10/2002 | |
| JP | 3366565 B2 | 1/2003 | |
| JP | 2003-187061 A | 7/2003 | |
| JP | 2004-056517 A | 2/2004 | |
| JP | 2004-227228 A | 8/2004 | |
| JP | 2006-345132 A | 12/2006 | |
| JP | 2007-324708 A | 12/2007 | |
| JP | 2009-081627 A | 4/2009 | |
| JP | 2011-511533 A | 4/2011 | |
| JP | 2011-511536 A | 4/2011 | |
| JP | 5421928 B2 | 2/2014 | |
| JP | 5631326 B2 | 11/2014 | |
| JP | 5649575 B2 | 1/2015 | |
| JP | 2015-514371 A | 5/2015 | |
| MX | 316118 | 12/2013 | |
| MX | 322251 | 7/2014 | |
| NZ | 587100 B | 10/2013 | |
| NZ | 587101 B | 10/2013 | |
| NZ | 591486 B | 1/2014 | |
| NZ | 592781 B | 3/2014 | |
| PH | 1-2010-501704 | 2/2014 | |
| PH | 1-2010-501705 | 2/2015 | |
| WO | WO-1999/17517 A1 | 4/1999 | |
| WO | WO-2001/063894 A2 | 8/2001 | |
| WO | WO-2006/124113 A2 | 11/2006 | |
| WO | WO-2009/097018 A1 | 8/2009 | |
| WO | WO-2010/053701 A2 | 5/2010 | |
| WO | WO-2011/081514 A1 | 7/2011 | |
| WO | WO-2019067044 A1 * | 4/2019 | G06N 20/00 |

OTHER PUBLICATIONS

Yongho Kim and Eric T Matson, A Realistic Decision Making for Task Allocation in Heterogeneous Multi-agent Systems, The 2nd International Workshop on Communication for Humans, Agents, Robots, Machines and Sensors, 2016. (Year: 2016).*

Afiniti, "Afiniti® Enterprise Behavioral Pairing™ Improves Contact Center Performance," White Paper, retreived online from URL: <http://www.afinitit,com/wp-content/uploads/2016/04/Afiniti_White-Paper_Web-Email.pdf> 11 pages (2016).

Anonymous. (2006) "Performance Based Routing in Profit Call Centers," The Decision Makers' Direct, located at www.decisioncraft.com, Issue Jun. 2002 (3 pages).

Chen, G., et al., "Enhanced Locality Sensitive Clustering in High Dimensional Space", Transactions on Electrical and Electronic Materials, vol. 15, No. 3, Jun. 25, 2014, pp. 125-129 (5 pages).

Cleveland, William S., "Robust Locally Weighted Regression and Smoothing Scatterplots," Journal of the American Statistical Association, vol. 74, No. 368, Dec. 1979, pp. 829-836 (8 pages).

Cormen, T.H., et al., "Introduction to Algorithms", Third Edition, Chapter 26 and 29, 2009, (116 pages).

Gans, N. et al., "Telephone Call Centers: Tutorial, Review and Research Prospects," Manufacturing & Service Operations Management, vol. 5, No. 2, 2003, pp. 79-141, (84 pages).

Ioannis Ntzoufras "Bayesian Modeling Using Winbugs An Introduction", Department of Statistics, Athens University of Economics and Business, Wiley-Interscience, A John Wiley & Sons, Inc., Publication, Chapter 5, Jan. 1, 2007, pp. 155-220 (67 pages).

Koole, G. (2004). "Performance Analysis and Optimization in Customer Contact Centers," Proceedings of the Quantitative Evaluation of Systems, First International Conference, Sep. 27-30, 2004 (4 pages).

Koole, G. et al., "An Overview of Routing and Staffing Algorithms in Multi-Skill Customer Contact Centers," Manuscript, Mar. 6, 2006, (42 pages).

Nocedal, J. and Wright, S. J., "Numerical Optimization," Chapter 16 Quadratic Programming, 2006, pp. 448-496 (50 pages).

Ntzoufras, "Bayesian Modeling Using Winbugs". Wiley Interscience, Chapter 5, Normal Regression Models, Oct. 18, 2007, Redacted version, pp. 155-220 (67 pages).

Press, W. H. and Rybicki, G. B., "Fast Algorithm for Spectral Analysis of Unevenly Sampled Data," The Astrophysical Journal, vol. 338, Mar. 1, 1989, pp. 277-280 (4 pages).

Riedmiller, M. et al. (1993). "A Direct Adaptive Method for Faster Back Propagation Learning: The RPROP Algorithm," 1993 IEEE International Conference on Neural Networks, San Francisco, CA, Mar. 28-Apr. 1, 1993, 1:586-591.

Stanley et al., "Improving call center operations using performance-based routing strategies," Calif. Journal of Operations Management, 6(1), 24-32, Feb. 2008; retrieved from http://userwww.sfsu.edu/saltzman/Publist.html.

International Preliminary Report on Patentability issued in connection with PCT Application No. PCT/US2009/066254 dated Jun. 14, 2011 (6 pages).

International Search Report and Written Opinion issued by the European Patent Office as International Searching Authority for International Application No. PCT/IB2016/001762 dated Feb. 20, 2017 (15 pages).

International Search Report and Written Opinion issued by the European Patent Office as International Searching Authority for International Application No. PCT/IB2016/001776 dated Mar. 3, 2017 (16 pages).

International Search Report and Written Opinion issued by the European Patent Office as International Searching Authority for International Application No. PCT/IB2017/000570 dated Jun. 30, 2017 (13 pages).

International Search Report issued in connection with International Application No. PCT/US13/33268 dated May 31, 2013 (2 pages).

International Search Report issued in connection with PCT Application No. PCT/US/2009/054352 dated Mar. 12, 2010, 5 pages.

International Search Report issued in connection with PCT Application No. PCT/US2008/077042 dated Mar. 13, 2009 (3 pages).

International Search Report issued in connection with PCT Application No. PCT/US2009/031611 dated Jun. 3, 2009 (5 pages).

International Search Report issued in connection with PCT Application No. PCT/US2009/066254 dated Feb. 24, 2010 (4 pages).

International Search Report issued in connection with PCT/US2009/061537 dated Jun. 7, 2010 (5 pages).

International Search Report issued in connection with PCT/US2013/033261 dated Jun. 14, 2013 (3 pages).

International Search Report issued in connection with PCT/US2013/33265 dated Jul. 9, 2013 (2 pages).

Written Opinion of the International Searching Authority issued in connection with International Application No. PCT/US13/33268 dated May 31, 2013, 7 pages.

Written Opinion of the International Searching Authority issued in connection with PCT Application No. PCT/US/2009/054352 dated Mar. 12, 2010, 5 pages.

Written Opinion of the International Searching Authority issued in connection with PCT Application No. PCT/US2008/077042 dated Mar. 13, 2009, 6 pages.

(56) References Cited

OTHER PUBLICATIONS

Written Opinion of the International Searching Authority issued in connection with PCT Application No. PCT/US2009/031611 dated Jun. 3, 2009, 7 pages.
Written Opinion of the International Searching Authority issued in connection with PCT Application No. PCT/US2009/066254 dated Feb. 24, 2010, 5 pages.
Written Opinion of the International Searching Authority issued in connection with PCT/US2009/061537 dated Jun. 7, 2010, 10 pages.
Written Opinion of the International Searching Authority issued in connection with PCT/US2013/033261 dated Jun. 14, 2013, 7 pages.
Written Opinion of the International Searching Authority issued in connection with PCT/US2013/33265 dated Jul. 9, 2013, 7 pages.

* cited by examiner

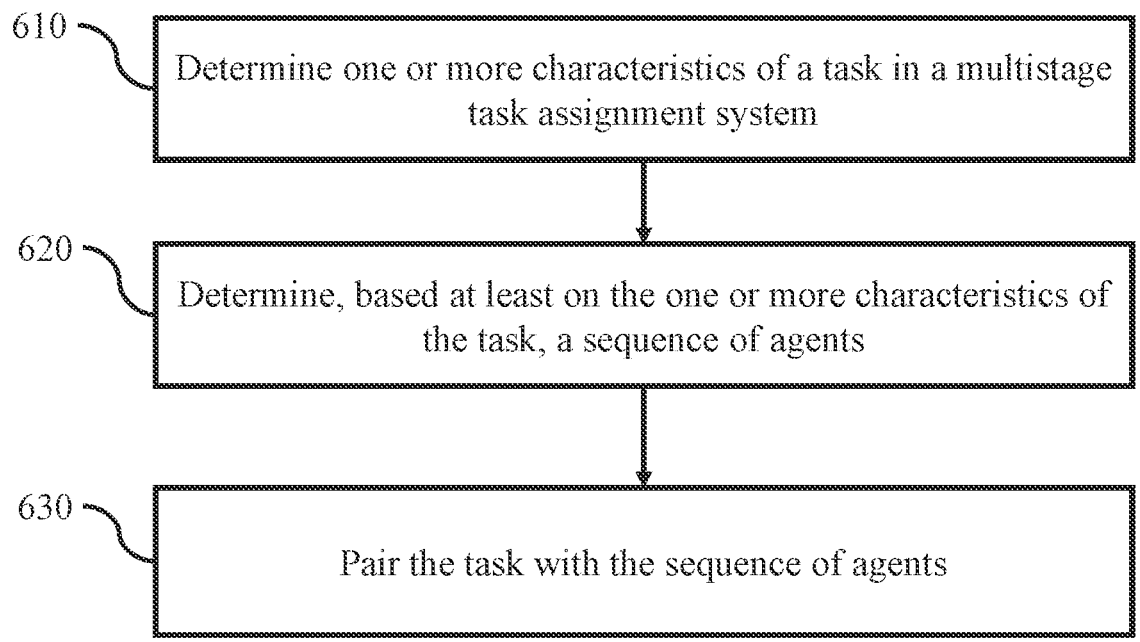

TECHNIQUES FOR BEHAVIORAL PAIRING IN A MULTISTAGE TASK ASSIGNMENT SYSTEM

CROSS-REFERENCE TO RELATED APPLICATIONS

This patent application is a continuation of U.S. patent application Ser. No. 16/209,295, filed on Dec. 4, 2018, which is hereby incorporated by reference herein in its entirety.

FIELD OF THE DISCLOSURE

This disclosure generally relates to behavioral pairing and, more particularly, to techniques for behavioral pairing in a multistage task assignment system.

BACKGROUND OF THE DISCLOSURE

A typical task assignment system algorithmically assigns tasks arriving at the task assignment system to agents available to handle those tasks. At times, the task assignment system may have agents available and waiting for assignment to tasks. At other times, the task assignment system may have tasks waiting in one or more queues for an agent to become available for assignment.

In some typical task assignment systems, tasks are assigned to agents ordered based on time of arrival, and agents receive tasks ordered based on the time when those agents became available. This strategy may be referred to as a "first-in, first-out," "FIFO," or "round-robin" strategy. For example, in an "L2" environment, multiple tasks are waiting in a queue for assignment to an agent. When an agent becomes available, the task at the head of the queue would be selected for assignment to the agent.

Some task assignment systems prioritize some types of tasks ahead of other types of tasks. For example, some tasks may be high-priority tasks, while other tasks are low-priority tasks. Under a FIFO strategy, high-priority tasks will be assigned ahead of low-priority tasks.

In other typical task assignment systems, a performance-based routing (PBR) strategy for prioritizing higher-performing agents for task assignment may be implemented. Under PBR, for example, the highest-performing agent among available agents receives the next available task. Other PBR and PBR-like strategies may make assignments using specific information about agents but without necessarily relying on specific information about tasks.

In some typical task assignment systems, a behavioral pairing (BP) model may be generated based on historical task-agent assignment data to optimize performance of the task assignment system. For example, in a contact center environment, the BP model may be calibrated to optimize revenue in a sales queue or to reduce average handle time in a sales or customer service queue.

In some task assignment systems, such as Enterprise Resource Planning (ERP) systems (e.g., a prescription medication fulfillment system), a single task (e.g., a prescription order) may require multiple stages of processing handled by multiple types of agents.

In view of the foregoing, it may be understood that there may be a need for a behavioral pairing model that can optimize a multistage task assignment system.

SUMMARY OF THE DISCLOSURE

Techniques for behavioral pairing in a multistage task assignment system are disclosed. In one particular embodiment, the techniques may be realized as a method for behavioral pairing in a multistage task assignment system comprising: determining, by at least one computer processor communicatively coupled to and configured to operate in the multistage task assignment system, one or more characteristics of a task; determining, by the at least one computer processor and based at least on the one or more characteristics of the task, a sequence of agents; and pairing, by the at least one computer processor, the task with the sequence of agents.

In accordance with other aspects of this particular embodiment, the multistage task assignment system may be a contact center system or a prescription medication fulfillment system.

In accordance with other aspects of this particular embodiment, determining the sequence of agents may comprise improving a performance of the multistage task assignment system.

In accordance with other aspects of this particular embodiment, determining the sequence of agents may comprise using a behavioral pairing strategy.

In accordance with other aspects of this particular embodiment, the sequence of agents may have a lower expected performance than another sequence of agents over a short period of time but a higher expected overall performance over a longer period of time.

In accordance with other aspects of this particular embodiment, determining the sequence of agents may comprise optimizing the multistage task assignment system to reduce an average total handle time for the task over multiple stages.

In another particular embodiment, the techniques may be realized as a system for behavioral pairing in a multistage task assignment system comprising at least one computer processor communicatively coupled to and configured to operate in the multistage task assignment system, wherein the at least one computer processor is further configured to perform the steps in the above-described method.

In another particular embodiment, the techniques may be realized as an article of manufacture for behavioral pairing in a multistage task assignment system comprising a non-transitory processor readable medium and instructions stored on the medium, wherein the instructions are configured to be readable from the medium by at least one computer processor communicatively coupled to and configured to operate in the multistage task assignment system and thereby cause the at least one computer processor to operate so as to perform the steps in the above-described method.

The present disclosure will now be described in more detail with reference to particular embodiments thereof as shown in the accompanying drawings. While the present disclosure is described below with reference to particular embodiments, it should be understood that the present disclosure is not limited thereto. Those of ordinary skill in the art having access to the teachings herein will recognize additional implementations, modifications, and embodiments, as well as other fields of use, which are within the scope of the present disclosure as described herein, and with respect to which the present disclosure may be of significant utility.

BRIEF DESCRIPTION OF THE DRAWINGS

To facilitate a fuller understanding of the present disclosure, reference is now made to the accompanying drawings, in which like elements are referenced with like numerals.

These drawings should not be construed as limiting the present disclosure, but are intended to be illustrative only.

FIG. 6 shows a flow diagram of a multistage task assignment method according to embodiments of the present disclosure.

DETAILED DESCRIPTION

Figure 1:
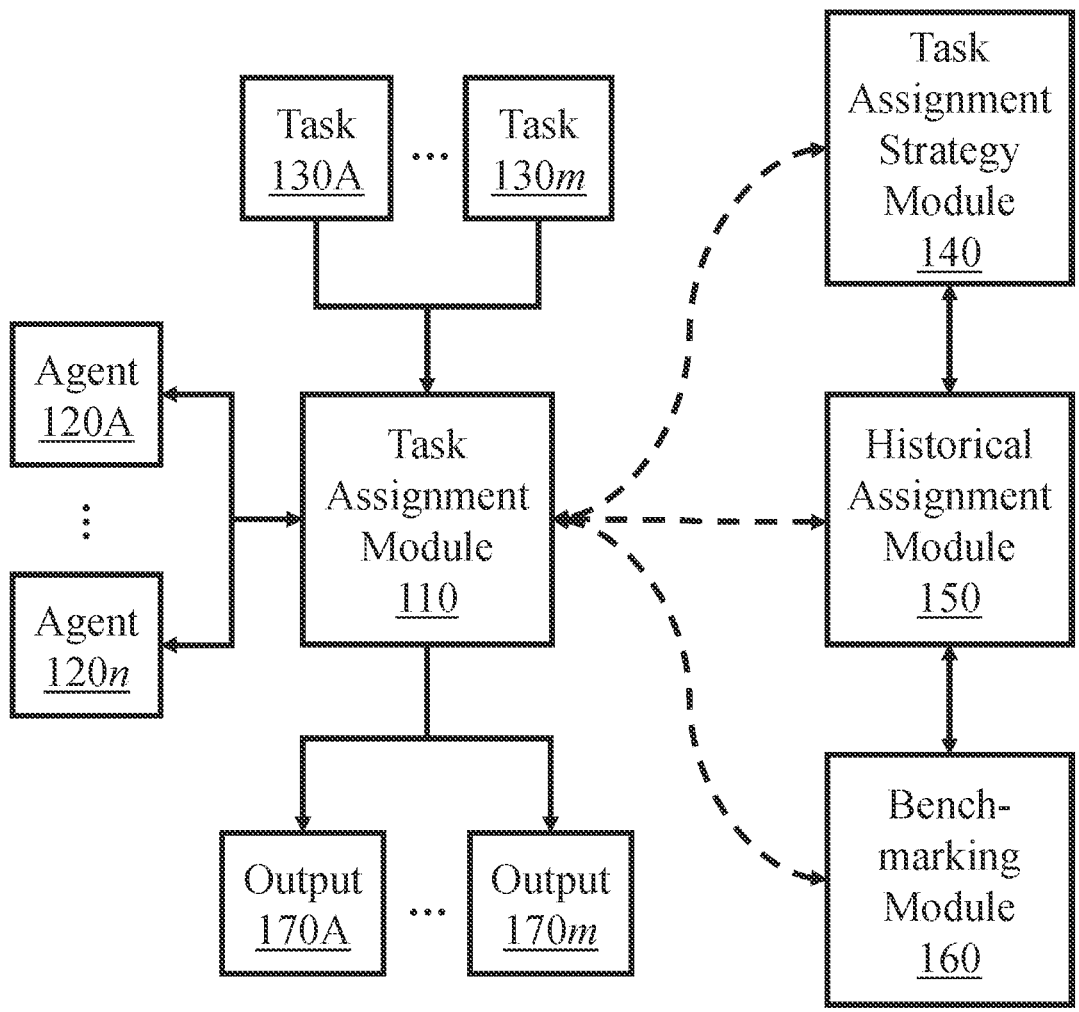
FIG. 1 shows a block diagram of a single-stage task assignment system according to embodiments of the present disclosure.

A typical task assignment system algorithmically assigns tasks arriving at the task assignment system to agents available to handle those tasks. At times, the task assignment system may have agents available and waiting for assignment to tasks. At other times, the task assignment system may have tasks waiting in one or more queues for an agent to become available for assignment.

In some typical task assignment systems, tasks are assigned to agents ordered based on time of arrival, and agents receive tasks ordered based on the time when those agents became available. This strategy may be referred to as a "first-in, first-out," "FIFO," or "round-robin" strategy. For example, in an "L2" environment, multiple tasks are waiting in a queue for assignment to an agent. When an agent becomes available, the task at the head of the queue would be selected for assignment to the agent.

Some task assignment systems prioritize some types of tasks ahead of other types of tasks. For example, some tasks may be high-priority tasks, while other tasks are low-priority tasks. Under a FIFO strategy, high-priority tasks may be assigned ahead of low-priority tasks.

In other typical task assignment systems, a performance-based routing (PBR) strategy for prioritizing higher-performing agents for task assignment may be implemented. Under PBR, for example, the highest-performing agent among available agents receives the next available task. Other PBR and PBR-like strategies may make assignments using specific information about agents but without necessarily relying on specific information about tasks.

In some typical task assignment systems, a behavioral pairing (BP) model may be generated based on historical task-agent assignment data to optimize performance of the task assignment system. For example, in a contact center environment, the BP model may be calibrated to optimize revenue in a sales queue or to reduce average handle time in a sales or customer service queue.

In some task assignment systems, such as Enterprise Resource Planning (ERP) systems (e.g., a prescription medication fulfillment system), a single task (e.g., a prescription order) may require multiple stages of processing handled by multiple types of agents.

In view of the foregoing, it may be understood that there may be a need for a behavioral pairing model that can optimize a multistage task assignment system.

The description herein describes network elements, computers, and/or components of a system and method for benchmarking pairing strategies in a task assignment system that may include one or more modules. As used herein, the term "module" may be understood to refer to computing software, firmware, hardware, and/or various combinations thereof. Modules, however, are not to be interpreted as software which is not implemented on hardware, firmware, or recorded on a non-transitory processor readable recordable storage medium (i.e., modules are not software per se). It is noted that the modules are exemplary. The modules may be combined, integrated, separated, and/or duplicated to support various applications. Also, a function described herein as being performed at a particular module may be performed at one or more other modules and/or by one or more other devices instead of or in addition to the function performed at the particular module. Further, the modules may be implemented across multiple devices and/or other components local or remote to one another. Additionally, the modules may be moved from one device and added to another device, and/or may be included in both devices.

FIG. 1 shows a block diagram of a single-stage task assignment system 100 according to embodiments of the present disclosure. The single-stage task assignment system 100 may include a task assignment module 110. The task assignment module 110 may include a switch or other type of routing hardware and software for helping to assign tasks among various agents, including queuing or switching components or other Internet-, cloud-, or network-based hardware or software solutions.

The task assignment module 110 may receive incoming tasks. In the example of FIG. 1, the task assignment module 110 receives m tasks over a given period, tasks 130A-130m. Each of the m tasks may be assigned to an agent of the single-stage task assignment system 100 for servicing or other types of task processing. In the example of FIG. 1, n agents are available during the given period, agents 120A-120n. As each of the m tasks gets processed by one of the n agents, the task assignment module 110 may provide m outputs (or outcomes) 170A-170m corresponding to tasks 130A-130m. m and n may be arbitrarily large finite integers greater than or equal to one. In a real-world task assignment system, such as a contact center, there may be dozens, hundreds, etc. of agents logged into the contact center to interact with contacts during a shift, and the contact center may receive dozens, hundreds, thousands, etc. of contacts (e.g., calls) during the shift.

In some embodiments, a task assignment strategy module 140 may be communicatively coupled to and/or configured to operate in the single-stage task assignment system 100. The task assignment strategy module 140 may implement one or more task assignment strategies (or "pairing strategies") or one or more models of a task assignment strategy for assigning individual tasks to individual agents (e.g., pairing contacts with contact center agents). For a given task queue (e.g., a sales queue in a contact center system, a truck roll or field agent dispatch queue in a dispatch queue center, an insurance claim or subrogation case in a claim processing center, etc.), the task assignment strategy module 140 may implement more than one model for more than one condition or goal. For example, in a sales queue, one goal may be to increase overall revenue generated by agents processing tasks in the sales queue (e.g., talking to callers in a call center interested in buying services from the company of the agents). A second goal may be to reduce average handle time (AHT) for tasks (e.g., complete a sales call relatively quickly). Historical task-agent pairing data may be available (e.g., from historical assignment module 150, which is described below) that includes both revenue and duration information, and two different models or sets of models may be generated that are calibrated to their respective goals of increasing revenue or decreasing average handle time.

A variety of different task assignment strategies may be devised and implemented by the task assignment strategy module 140, and made available to the task assignment module 110 at runtime. In some embodiments, a FIFO strategy may be implemented in which, for example, the longest-waiting agent receives the next available task (in L1 environments) or the longest-waiting task is assigned to the next available task (in L2 environments). Other FIFO and FIFO-like strategies may make assignments without relying on information specific to individual tasks or individual agents.

In other embodiments, a PBR strategy for prioritizing higher-performing agents for task assignment may be implemented. Under PBR, for example, the highest-performing agent among available agents receives the next available task. Other PBR and PBR-like strategies may make assignments using information about specific agents but without necessarily relying on information about specific tasks or agents.

In yet other embodiments, a BP strategy may be used for optimally assigning tasks to agents using information about both specific tasks and specific agents. Various models of the BP strategy may be used, such as a diagonal model BP strategy, a payout matrix BP strategy, or a network flow BP strategy. These task assignment strategies and others are described in detail for the contact center context in, e.g., U.S. Pat. Nos. 9,300,802 and 9,930,180, which are hereby incorporated by reference herein. BP strategies may be applied in an "L1" environment (agent surplus, one task; select among multiple available/idle agents), an "L2" environment (task surplus, one available/idle agent; select among multiple tasks in queue), and an "L3" environment (multiple agents and multiple tasks; select among pairing permutations).

In some embodiments, the task assignment strategy module 140 may be configured to switch from one task assignment strategy to another task assignment strategy, or from one model of a task assignment strategy to another model of the task assignment strategy, in real time. A goal for optimizing the single-stage task assignment system 100 or a particular queue of the single-stage task assignment system 100 may change at runtime (i.e., in real time) based on conditions or parameters in the single-stage task assignment system 100 that can change at any moment. For example, a condition may be based on the size of the task queue. When the single-stage task assignment system 100 is operating in L1 (i.e., agent surplus), or the size of the task queue in L2 is less than (or equal to) a certain size (e.g., 5, 10, 20 tasks, etc.), the single-stage task assignment system 100 may operate with the goal of increasing revenue and the task assignment strategy module 140 may select a model or a set of models corresponding to that goal. When the single-stage task assignment system 100 detects that the size of the task queue in L2 is greater than (or equal to) a threshold size, the task assignment strategy module 140 may switch to operate with the goal of decreasing average handle time and switch to a model or set of models corresponding to the new goal. Examples of other goals may include improving customer satisfaction (e.g., customer satisfaction (CSAT) scores or Net Promoter Scores), increasing upgrade/cross-sell rates, increasing customer retention rates, decreasing AHT, etc. Example of other conditions or parameters may include switching between L1 and L2 (i.e., switching between agent surplus and task surplus conditions), unexpected reduction in capacity (e.g., sites/queues/agents workstations/server/switch failure or recovery), number of agents assigned to the task queue (or number of agents available/logged in/idle), schedule-based/cycling changes to the goals and models (which can be benchmarked similarly to benchmarking ON/OFF cycles between two pairing strategies, as described below), time of the day or amount of elapsed time (for schedule-based cycling of models and benchmarking), etc.

In some embodiments, an operator or manager of the single-stage task assignment system 100 may select or switch goals or models manually. In response to the operator's selection, the task assignment strategy module 140 may switch models in real time. In other embodiments, the task assignment strategy module 140 may monitor the single-stage task assignment system 100 for certain conditions or parameters and, in response to detecting particular changes in these conditions or parameters, may select or switch goals and models automatically. In yet other embodiments, the conditions that trigger switching the goals or models may be determined automatically as part of a super- or meta-model from analyzing historical task-agent assignment data (available from historical assignment module 150, which is described below).

In some embodiments, a historical assignment module 150 may be communicatively coupled to and/or configured to operate in the single-stage task assignment system 100 with other modules such as the task assignment module 110 and/or the task assignment strategy module 140. The historical assignment module 150 may be responsible for various functions such as monitoring, storing, retrieving, and/or outputting information about agent-task assignments that have already been made. For example, the historical assignment module 150 may monitor the task assignment module 110 to collect information about task assignments in a given period. Each record of a historical task assignment may include information such as an agent identifier, a task or task type identifier, outcome information, or a pairing strategy identifier (i.e., an identifier indicating whether a task assignment was made using a BP pairing strategy or some other pairing strategy such as a FIFO or PBR pairing strategy).

In some embodiments and for some contexts, additional information may be stored. For example, in a call center context, the historical assignment module 150 may also store information about the time a call started, the time a call ended, the phone number dialed, and the caller's phone number. For another example, in a dispatch center (e.g., "truck roll") context, the historical assignment module 150 may also store information about the time a driver (i.e., field agent) departs from the dispatch center, the route recommended, the route taken, the estimated travel time, the actual travel time, the amount of time spent at the customer site handling the customer's task, etc.

In some embodiments, the historical assignment module 150 may generate a pairing model or similar computer processor-generate model based on a set of historical assignments for a period of time (e.g., the past week, the past month, the past year, etc.), which may be used by the task assignment strategy module 140 to make task assignment recommendations or instructions to the task assignment module 110. In other embodiments, the historical assignment module 150 may send historical assignment information to another module such as the task assignment strategy module 140 or a benchmarking module 160, which is described next.

In some embodiments, the benchmarking module 160 may be communicatively coupled to and/or configured to operate in the single-stage task assignment system 100 with other modules such as the task assignment module 110 and/or the historical assignment module 150. The benchmarking module 160 may benchmark the relative performance of two or more pairing strategies (e.g., FIFO, PBR, BP, etc.) using historical assignment information, which may be received from, for example, the historical assignment module 150. In some embodiments, the benchmarking module 160 may perform other functions, such as establishing a benchmarking schedule for cycling among various pairing strategies, tracking cohorts (e.g., base and measurement groups of historical assignments), etc. Benchmarking is described in detail for the contact center context in, e.g., U.S. Pat. No. 9,712,676, which is hereby incorporated by reference herein.

In some embodiments, the benchmarking module 160 may output or otherwise report or use the relative performance measurements. The relative performance measurements may be used to assess the quality of the task assignment strategy to determine, for example, whether a different task assignment strategy (or a different pairing model) should be used, or to measure the overall performance (or performance gain) that was achieved within the single-stage task assignment system 100 while it was optimized or otherwise configured to use one task assignment strategy instead of another.

Figure 2:
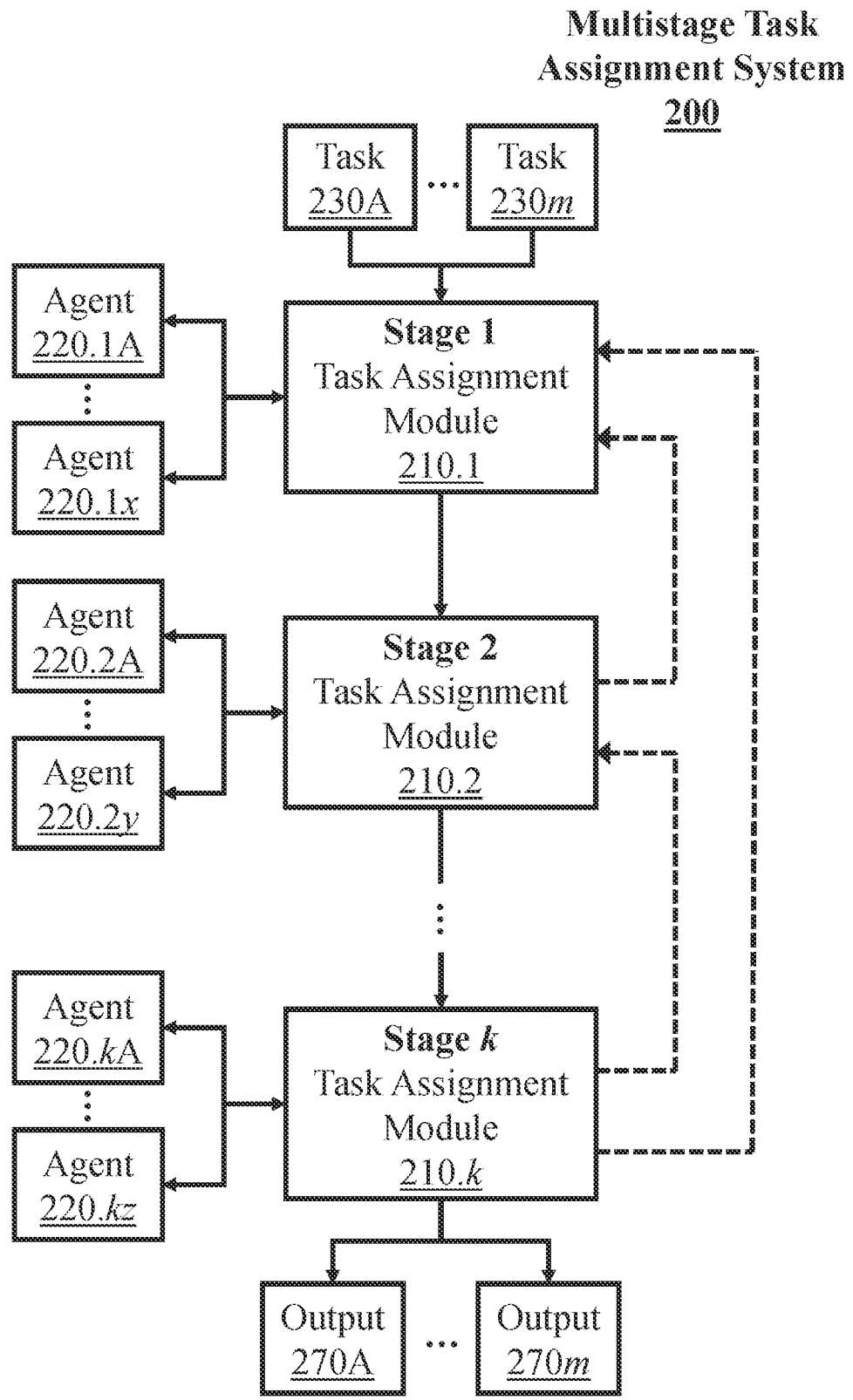
FIG. 2 shows a block diagram of a multistage task assignment system according to embodiments of the present disclosure.

FIG. 2 shows a block diagram of a multistage task assignment system 200 according to embodiments of the present disclosure. The multistage task assignment system 200 may include k task assignment modules, task assignment modules 210.1-210.$k$, corresponding to k stages, stages 1-k. Each of the task assignment modules 210 may include at least one switch or other type of routing hardware and software for helping to assign tasks among various agents at each stage of the stages 1-k, including queuing or switching components or other Internet-, cloud-, or network-based hardware or software solutions. k may be an arbitrarily large finite integer greater than or equal to one.

Each of the task assignment modules 210 may receive incoming tasks. In the example of FIG. 2, the task assignment modules 210 receive m tasks over a given period, tasks 230A-230$m$. Each of the m tasks may be assigned serially to an agent at each stage of the stages 1-k, by the corresponding task assignment modules 210.1-210.$k$, for servicing or other types of task processing. For example, during the given time period, x agents, agents 220.1A-220.1$x$, may be available at stage 1; y agents, agents 220.2A-220.2$y$, may be available at stage 2; and z agents, agents 220.$k$A-220.$ky$ may be available at stage k. As each of the m tasks gets processed by an agent at a stage, the outcome may be provided to a subsequent stage.

In some embodiments, an agent may kick back a task to any of earlier stages (as illustrated by dotted arrows in FIG. 2) as a type of exception handling or exception processing. Once a task has undergone servicing or processing at every stage, the task assignment modules 210 may provide corresponding outputs. For example, the task assignment modules 210 may provide m outputs (or outcomes) 270A-270$m$ corresponding to tasks 230A-230$m$. In some embodiments, one or more of the stages 1-k may be skipped. In some embodiments, agents may have more than one role or skillset. In some embodiments, agents may be paired multiple times in a sequence for the same task. m, x, y, and z may be arbitrarily large finite integers greater than or equal to one. In a real-world task assignment system, such as a prescription medication fulfillment system, there may be dozens, hundreds, etc. of clerks, technicians, and pharmacists logged into stages of the prescription medication fulfillment system to process prescription orders during a shift, and the prescription medication fulfillment system may receive dozens, hundreds, thousands, etc. of prescription orders during the shift.

In some embodiments, when a task becomes subject to an exception (e.g., an exception to any stage or a kick back to an earlier stage) or another process step requiring intervention by another type of agent (e.g., flagging a task for review or approval by a supervisory agent prior to completion), the task assignment modules 210 may assign the task to a particular stage (e.g., a particular type of agent) and/or a particular agent assigned to the particular stage. In some embodiments, the stage handling the exception event may have a queue of tasks awaiting exception handling and/or ordinary handling. In these embodiments, the task assignment modules 210 may assign tasks out of queue order. For example, the task assignment modules 210 may assign the task subject to an exception earlier than another ordinary task or another task subject to an exception, so as to improve the overall performance of the task assignment system such as the productivity or efficiency of the task assignment system according to one or more performance metrics.

In some embodiments, although not shown in FIG. 2, each of the task assignment modules 210.1-210.$k$ may be communicatively coupled to one or more of a task assignment strategy module (e.g., task assignment strategy module 140), a historical assignment module (e.g., historical assignment module 150), and a benchmarking module (e.g., benchmarking module 160). In other embodiments, the task assignment modules 210.1-210.$k$ may be communicatively coupled to the same task assignment strategy module, historical assignment module, and/or benchmarking module.

For each or all of the stages 1-k of the multistage task assignment system 200, a task assignment strategy module may implement one or more task assignment strategies or pairing strategies (e.g., FIFO, PBR, BP, etc.) or one more models of a task assignment strategy for assigning individual tasks to individual agents. In some embodiments, a task assignment strategy module may be configured to switch from one task assignment strategy to another task assignment strategy, or from one model of a task assignment strategy to another model of the task assignment strategy, in real time to adapt to real-time changes in goals in optimizing each stage or all stages of the multistage task assignment system 200.

At each or all of the stages 1-k of the multistage task assignment system 200, a historical assignment module may monitor, store, retrieve, and/or output information about agent-task assignments that have already been made. A historical assignment module may generate a pairing model or similar computer processor-generate model based on a set of historical assignments for a period of time (e.g., the past week, the past month, the past year, etc.), which may be used by a task assignment strategy module to make task assignment recommendations or instructions to each or all of the task assignment module 210.1-210.$k$. A historical assignment module may send historical assignment information to another module such as a task assignment strategy module or a benchmarking module.

At each or all of the stages 1-k of the multistage task assignment system 200, a benchmarking module may benchmark the relative performance of two or more pairing strategies (e.g., FIFO, PBR, BP, etc.) using historical assignment information, which may be received from, for example, a historical assignment module. A benchmarking module may perform other functions, such as establishing a benchmarking schedule for cycling among various pairing strategies, tracking cohorts, etc. A benchmarking module may output or otherwise report or use the relative performance measurements. The relative performance measurements may be used to assess the quality of the task assignment strategy to determine, for example, whether a different task assignment strategy (or a different pairing model) should be used, or to measure the overall performance (or performance gain) that was achieved within the multistage task assignment system 200 or within each of the stages 1-k, while it was optimized or otherwise configured to use one task assignment strategy instead of another.

Figure 3:
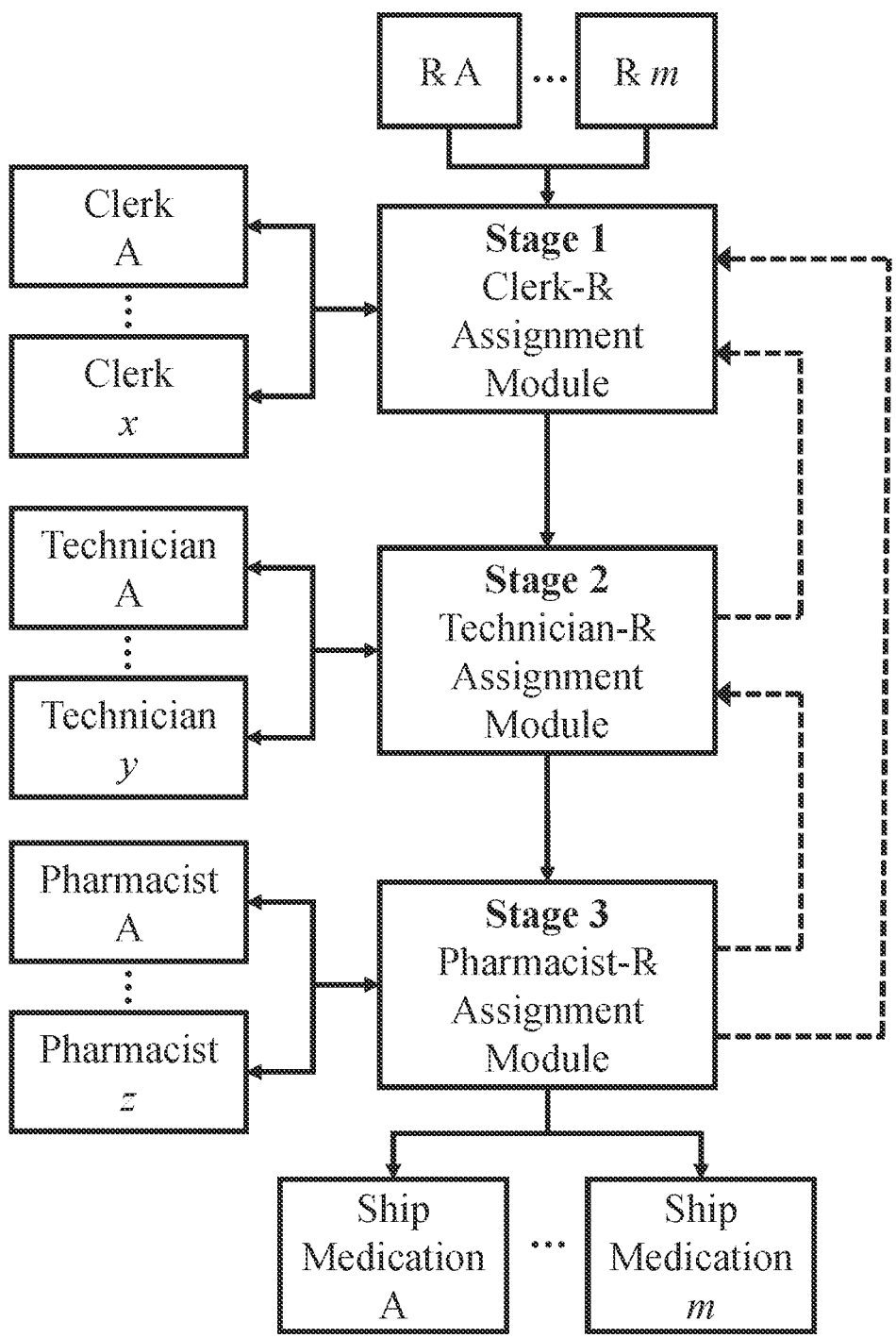
FIG. 3 shows a block diagram of a prescription medication fulfillment system according to embodiments of the present disclosure.

FIG. 3 shows a block diagram of a prescription medication fulfillment system 300 according to embodiments of the present disclosure. In the example of FIG. 3, the prescription medication fulfillment system 300 includes three stages, with three types of agents—clerks, technicians, and pharmacists. Clerks typically identify patients and perform other generic preprocessing or clerical functions such as verifying names and address information, updating patient identification numbers, verifying insurance benefits, etc. Technicians typically review scripts for technical information such as the names and types of drug, dose, generic alternatives, interactions with other medications, etc. Pharmacists typically review and approve finalized scripts. Accordingly, the prescription medication fulfillment system 300 is shown to have three stages, stages 1-3, one for each of the three types of agents.

In the example of FIG. 3, the prescription medication fulfillment system 300 receives m prescription orders, ℞ A-℞ m. The m prescription orders may be in the form of conventional paper prescriptions by doctors or physicians, electronic prescriptions or e-scripts, mail/web orders, physicians' or doctors' offices call-in, etc. In a typical sequence, each of the prescription orders ℞ A-℞ m proceeds through the three stages from getting a script to shipping the associated medication(s). First, the clerk-℞ assignment module assigns the script to one of x clerks. After processing by the clerk, the technician-℞ assignment module assigns the script to one of y technicians. After processing by the technician, the pharmacist-℞ assignment module assigns the script for processing and approval by one of z pharmacists, after which the medication(s) associated with the script may be shipped, delivered, or otherwise given to the patient.

Each type of agent may reject or kick back a prescription order to an earlier stage (as illustrated by the dotted arrows in FIG. 3) as a type of exception handling or exception processing. For example, if a technician at stage 2 cannot look up the patient information, the order may get kicked back to a clerk at stage 1. In some embodiments, if the technician cannot read the dosage, the technician may initiate an outbound call the to the prescribing physician or kick back the order to the clerk to make the call. If a pharmacist at stage 3 detects a potentially dangerous interaction with another prescription, or any other number of issues, the pharmacist may reject the script or kick back the script to either a technician at stage 2 or a clerk at stage 1. These rejections and processing delays may increase the time it takes from ordering the prescription to fulfilling the order and shipping the medications. Different types of prescription orders may require different sequences of agents (e.g., technician only, or clerk and pharmacist, or clerk/technician/pharmacist, or different orders of agents (clerk/technician or technician/clerk)).

In some embodiments, when a prescription order becomes subject to an exception (e.g., an exception to any stage or a kick back to an earlier stage), the assignment modules at stages 1-3 may assign the prescription order to a particular stage (e.g., a clerk, technician, or a pharmacist) and/or a particular clerk, technician, or pharmacist, assigned to the particular stage. In some embodiments, the stage handling the exception event may have a queue of prescription orders awaiting exception handling and/or ordinary handling. In these embodiments, the assignment modules at stages 1-3 may assign prescription orders out of queue order. For example, the assignment modules at stages 1-3 may assign the prescription order subject to an exception earlier than another ordinary prescription order or another prescription order subject to an exception, so as to improve the overall performance of the prescription medication fulfillment system such as the productivity or efficiency of the prescription medication fulfillment system according to one or more performance metrics.

In some embodiments, although not shown in FIG. 3, each of the clerk-℞, technician-℞, and pharmacist-℞ assignment modules may be communicatively coupled to one or more of a task assignment strategy module, a historical assignment module, and a benchmarking module. In other embodiments, the clerk-℞, technician-℞, and pharmacist-℞ assignment modules may be communicatively coupled to the same task assignment strategy module, historical assignment module, and/or benchmarking module.

For each or all of the stages 1-3 of the prescription medication fulfillment system 300, a task assignment strategy module may implement one or more task assignment strategies or pairing strategies (e.g., FIFO, PBR, BP, etc.) or one more models of a task assignment strategy for assigning prescription orders to individual clerks, technicians, or pharmacists. A task assignment strategy module may choose the most appropriate pairing strategy to increase accuracy, decrease kick-back rate (i.e., exception handling rate), decrease error rate, increase customer satisfaction, or decrease handle/processing time. In some embodiments, a task assignment strategy module may be configured to switch from one task assignment strategy to another task assignment strategy, or from one model of a task assignment strategy to another model of the task assignment strategy, in real time to adapt to real-time changes in goals in optimizing each stage or all stages of the prescription medication fulfillment system 300.

At each or all of the stages 1-3 of the prescription medication fulfillment system 300, a historical assignment module may monitor, store, retrieve, and/or output information about clerk/technician/pharmacist-prescription order assignments that have already been made. A historical assignment module may generate a pairing model or similar computer processor-generate model based on a set of historical assignments for a period of time (e.g., the past week, the past month, the past year, etc.), which may be used by a task assignment strategy module to make task assignment recommendations or instructions to each or all of the clerk-℞, technician-℞, and pharmacist-℞ assignment modules. A historical assignment module may send historical assignment information to another module such as a task assignment strategy module or a benchmarking module.

At each or all of the stages 1-3 of the prescription medication fulfillment system 300, a benchmarking module may benchmark the relative performance of two or more pairing strategies (e.g., FIFO, PBR, BP, etc.) using historical assignment information, which may be received from, for example, a historical assignment module. A benchmarking module may perform other functions, such as establishing a benchmarking schedule for cycling among various pairing strategies, tracking cohorts, etc. A benchmarking module may output or otherwise report or use the relative performance measurements. The relative performance measurements may be used to assess the quality of the task assignment strategy to determine, for example, whether a different task assignment strategy (or a different pairing model) should be used, or to measure the overall performance (or performance gain) that was achieved within the prescription medication fulfillment system 300 or within each of the stages 1-3, while it was optimized or otherwise configured to use one task assignment strategy instead of another.

Figure 4:
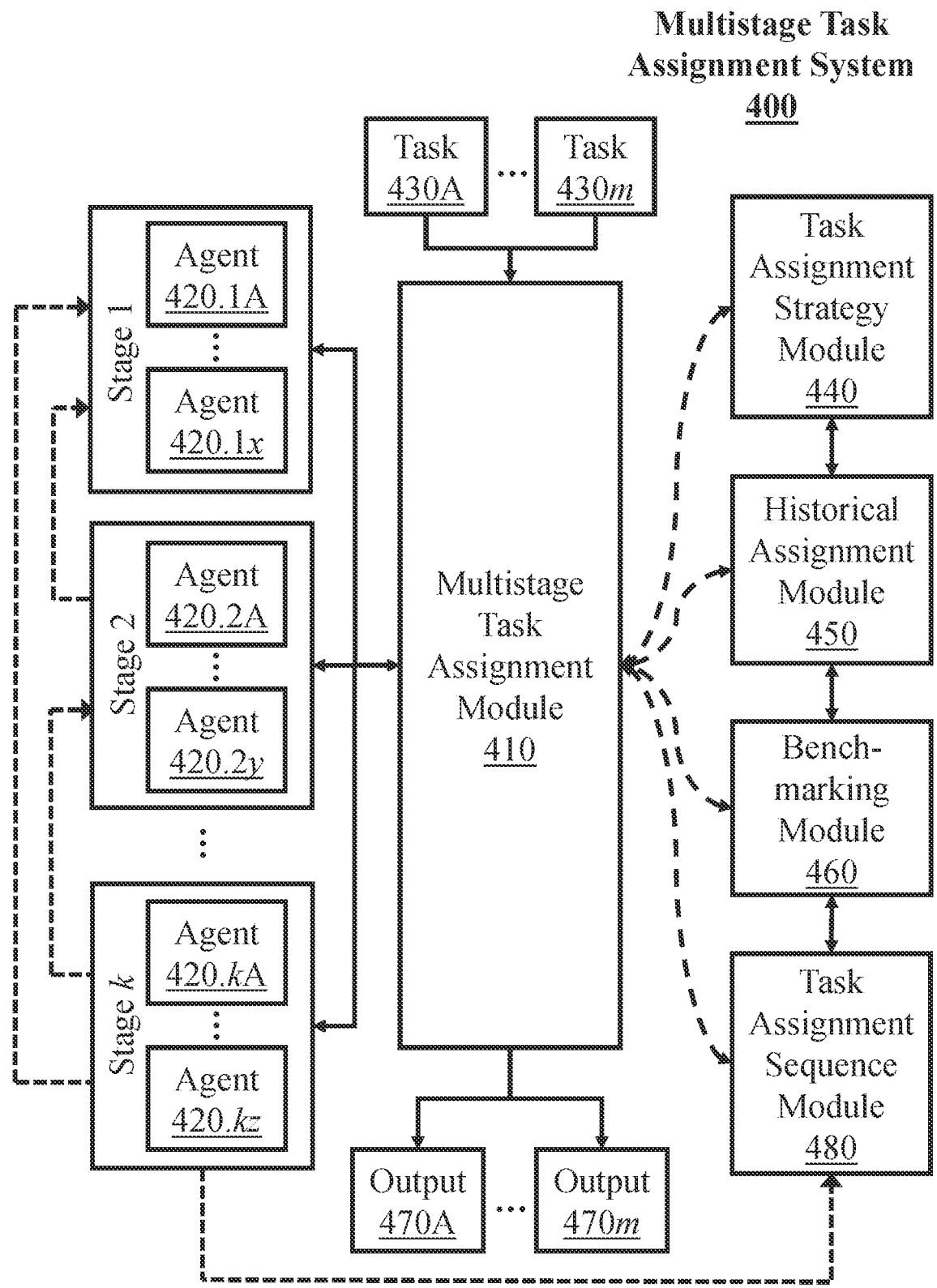
FIG. 4 shows a block diagram of a multistage task assignment system according to embodiments of the present disclosure.

FIG. 4 shows a block diagram of a multistage task assignment system 400 according to embodiments of the present disclosure. The multistage task assignment system 400 may include a multistage task assignment module 410. The multistage task assignment module 410 may include at least one switch or other type of routing hardware and software for helping to assign tasks among various agents at each stage of stages 1-k, including queuing or switching components or other Internet-, cloud-, or network-based hardware or software solutions. k may be an arbitrarily large finite integer greater than or equal to one.

The multistage task assignment module 410 may receive incoming tasks. In the example of FIG. 4, the multistage task assignment module 410 receives m tasks over a given period, tasks 430A-430m. The multistage task assignment module 410 may assign each of the m tasks to an agent in any stage of the stages 1-k, in any sequence, for servicing or other types of task processing. During the given time period, x agents, agents 420.1A-420.1x, may be available at stage 1; y agents, agents 420.2A-420.2y, may be available at stage 2; and z agents, agents 420.kA-420.ky may be available at stage k. As each of the m tasks gets processed by a desired or optimized sequence of agents from any or all of the stages 1-k, the multistage task assignment module 410 may provide a corresponding output. For example, the multistage task assignment module 410 may provide m outputs (or outcomes) 470A-470m corresponding to tasks 430A-430m. In some embodiments, one or more of the stages 1-k may be skipped. In some embodiments, agents may have more than one role or skillset. In some embodiments, agents may be paired multiple times in a sequence for the same task. m, x, y, and z may be arbitrarily large finite integers greater than or equal to one.

In some embodiments, a task assignment strategy module 440 may be communicatively coupled to and/or configured to operate in the multistage task assignment system 400. The task assignment strategy module 440 may implement one or more task assignment strategies or pairing strategies (e.g., FIFO, PBR, BP, etc.) or one more models of a task assignment strategy for assigning individual tasks to individual agents in any of the stages 1-k. In some embodiments, the task assignment strategy module 440 may be configured to switch from one task assignment strategy to another task assignment strategy, or from one model of a task assignment strategy to another model of the task assignment strategy, in real time to adapt to real-time changes in goals in optimizing agent-task assignment at any of the stages 1-k of the multistage task assignment system 400. In some embodiment, pairing a task with a sequence of agents may have a lower expected performance than pairing the task with another sequence of agents over a short period of time, but a higher expected overall performance over a longer period of time.

In some embodiments, a historical assignment module 450 may be communicatively coupled to and/or configured to operate in the multistage task assignment system 400 with other modules such as the task assignment module 410 and/or the task assignment strategy module 440. The historical assignment module 450 may monitor, store, retrieve, and/or output information about agent-task assignments that have already been made at any of the stages 1-k. The historical assignment module 450 may generate a pairing model or similar computer processor-generate model based on a set of historical assignments for a period of time (e.g., the past week, the past month, the past year, etc.), which may be used by the task assignment strategy module 440 to make task assignment recommendations or instructions to the multistage task assignment module 410. The historical assignment module 450 may send historical assignment information to another module such as the task assignment strategy module 440 or a benchmarking module 460, which is described next.

In some embodiments, the benchmarking module 460 may be communicatively coupled to and/or configured to operate in the multistage task assignment system 400 with other modules such as the task assignment module 410 and/or the historical assignment module 450. The benchmarking module 460 may benchmark the relative performance of two or more pairing strategies (e.g., FIFO, PBR, BP, etc.) using historical assignment information, which may be received from, for example, the historical assignment module 450. The benchmarking module 460 may perform other functions, such as establishing a benchmarking schedule for cycling among various pairing strategies, tracking cohorts, etc. The benchmarking module 460 may output or otherwise report or use the relative performance measurements. The relative performance measurements may be used to assess the quality of the task assignment strategy to determine, for example, whether a different task assignment strategy (or a different pairing model) should be used, or to measure the overall performance (or performance gain) that was achieved when pairing tasks to agents from any of the stages 1-k, while the agent-task pairing was optimized or when one task assignment strategy instead of another was used for the agent-task pairing.

In some embodiments, a task assignment sequence module 480 may be communicatively coupled to and/or configured to operate in the multistage task assignment system 400 with other modules such as the task assignment module 410, the task assignment strategy module 440, the historical assignment module 450, and/or the benchmarking module 460. To account for differences in tasks 430A-430m, the task assignment sequence module 480 may optimize a sequence of agents from any or all of the stages 1-k to optimize the performance of the multistage task assignment system 400. For example, behavioral pairing may be used to pair a task with a sequence of agents (e.g., agent 420.1A from stage 1, followed by agent 420.2A from stage 2, . . . , followed by agent 420.kB from stage k). The task assignment sequence module 480 may provide the multistage task assignment module 410 with an optimal sequence based on information about the tasks 430A-430m and/or information from the task assignment strategy module 440, the historical assignment module 450, and/or the benchmarking module 460. Pairing an entire sequence (or multiple stages of an entire sequence) may improve upon the optimization of pairing single stages at a time in some environments, such as the multistage task assignment system 200.

In the example of FIG. 4, in addition to any agent from any of the stages 1-k being able to kick back a task to an earlier stage (as shown by the dotted arrows between the stages), any agent from any of the stages 1-k may also kick back a task to the task assignment sequence module 480 to trigger a reassignment of a task to a new sequence of agents.

In some embodiments (not shown), a task may be subject to other kinds of exception handling, triggering a reassignment of a task to a new agent within the current stage, to any of the other stages 1-k. A reassigned task subject to an exception may join a queue of ordinary tasks or other tasks subject to an exception, and the queued tasks may be assigned to agents within the stages out of queue order, so as to optimize the overall performance (e.g., productivity, efficiency) of the task assignment system according to one or more performance metrics.

Figure 5:
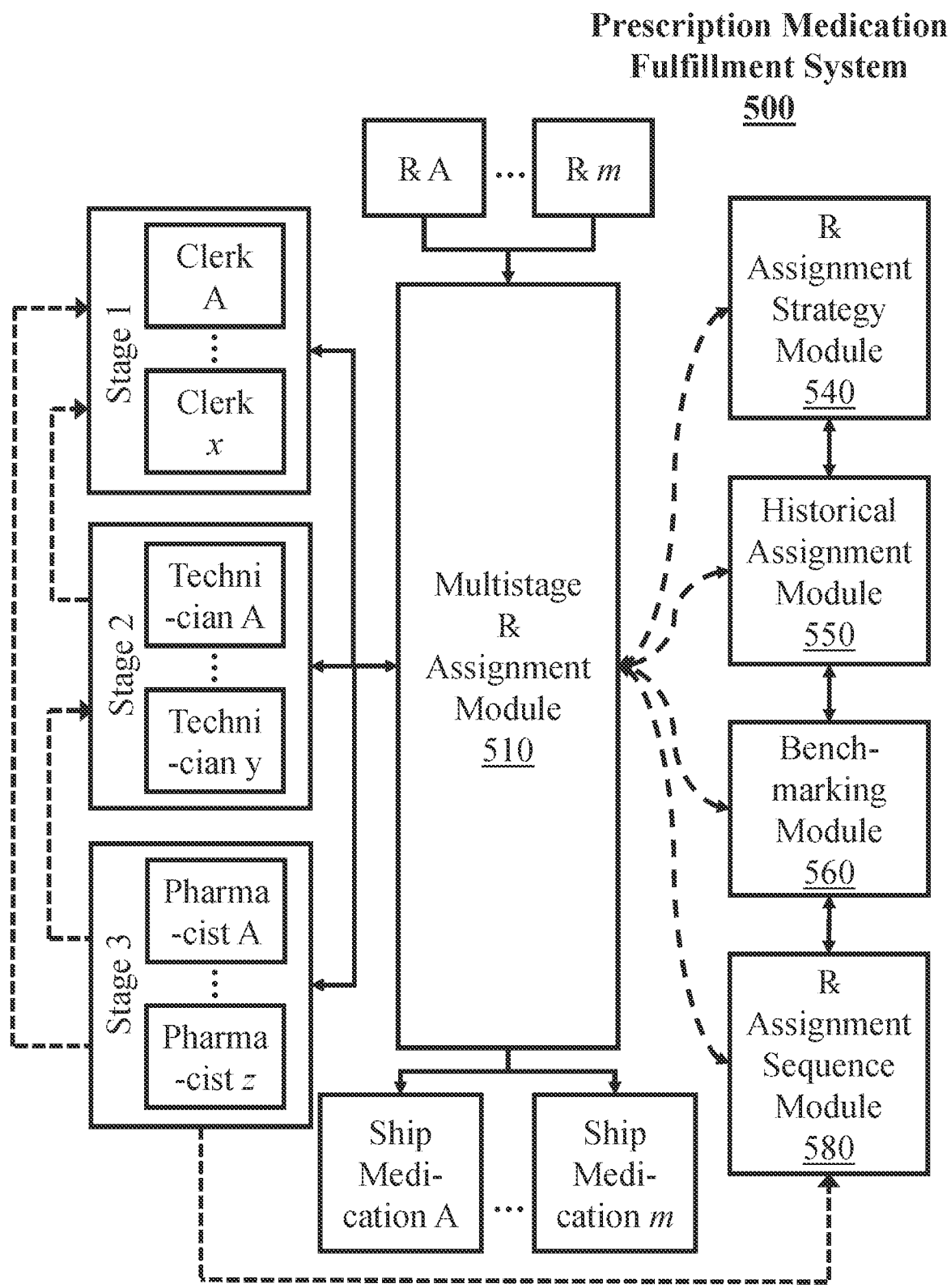
FIG. 5 shows a block diagram of a prescription medication fulfillment system according to embodiments of the present disclosure.

FIG. 5 shows a block diagram of a prescription medication fulfillment system 500 according to embodiments of the present disclosure. The prescription medication fulfillment system 500 includes three stages, with three types of agents—clerks, technicians, and pharmacists. The prescription medication fulfillment system 500 includes a multistage ℞ assignment module 510. The multistage ℞ assignment module 510 receives m prescription orders, ℞ ℞ A-℞ m. The multistage ℞ assignment module 510 assigns each of the m prescription orders to any of the x clerks in stage 1, y technicians in stage 2, and the z pharmacists in stage 3, in any sequence, such that medication A-medication m gets shipped, delivered, or otherwise given to corresponding patients. Such a configuration allows the prescription medication fulfillment system 500 to minimize the total handle time across all stages, "from script to ship." The prescription medication fulfillment system 500 may employ a multistage behavioral pairing algorithm to optimize the total handle time for all of the scripts over a period of time instead of optimizing individual handle times for each individual stage of each individual prescription order.

A ℞ assignment strategy module 540 is communicatively coupled to and/or configured to operate in the prescription medication fulfillment system 500. The ℞ assignment strategy module 540 may implement one or more ℞ assignment strategies or pairing strategies (e.g., FIFO, PBR, BP, etc.) or one more models of a ℞ assignment strategy for assigning individual ℞ to an individual clerk, technician, or pharmacist in any of the stages 1-3. The ℞ assignment strategy module 540 may be configured to switch from one ℞ assignment strategy to another ℞ assignment strategy, or from one model of a ℞ assignment strategy to another model of the ℞ assignment strategy, in real time to adapt to real-time changes in goals in optimizing clerk/technician/pharmacist-℞ assignment at any of the stages 1-3 of the prescription medication fulfillment system 500.

A historical assignment module 550 is communicatively coupled to and/or configured to operate in the prescription medication fulfillment system 500 with other modules such as the multistage ℞ assignment module 510 and/or the ℞ assignment strategy module 540. The historical assignment module 550 may monitor, store, retrieve, and/or output information about clerk/technician/pharmacist-℞ assignments that have already been made at any of the stages 1-3. The historical assignment module 550 may generate a pairing model or similar computer processor-generate model based on a set of historical assignments for a period of time (e.g., the past week, the past month, the past year, etc.), which may be used by the ℞ assignment strategy module 540 to make ℞ assignment recommendations or instructions to the multistage ℞ assignment module 510. The historical assignment module 550 may send historical assignment information to another module such as the ℞ assignment strategy module 540 or a benchmarking module 560, which is described next.

The benchmarking module 560 is communicatively coupled to and/or configured to operate in the prescription medication fulfillment system 500 with other modules such as the multistage ℞ assignment module 510 and/or the historical assignment module 550. The benchmarking module 560 may benchmark the relative performance of two or more pairing strategies (e.g., FIFO, PBR, BP, etc.) using historical assignment information, which may be received from, for example, the historical assignment module 550. The benchmarking module 560 may perform other functions, such as establishing a benchmarking schedule for cycling among various pairing strategies, tracking cohorts, etc. The benchmarking module 560 may output or otherwise report or use the relative performance measurements. The relative performance measurements may be used to assess the quality of the ℞ assignment strategy to determine, for example, whether a different ℞ assignment strategy (or a different pairing model) should be used, or to measure the overall performance (or performance gain) that was achieved when pairing a prescription to a clerk, a technician, and/or a pharmacist from any of the stages 1-3, while the clerk/technician/pharmacist-℞ pairing was optimized or when one ℞ assignment strategy instead of another was used for the clerk/technician/pharmacist-℞ pairing.

A ℞ assignment sequence module 580 is communicatively coupled to and/or configured to operate in the prescription medication fulfillment system 500 with other modules such as the multistage ℞ assignment module 510, the ℞ assignment strategy module 540, the historical assignment module 550, and/or the benchmarking module 560. To account for differences in the m prescription orders, ℞ ℞ A-℞ m, the ℞ assignment sequence module 580 may optimize a sequence of clerks, technicians, and/or pharmacists from any or all of the stages 1-3 to optimize the performance of the prescription medication fulfillment system 500. Any of the technicians and the pharmacists is able to kick back a prescription order to an earlier stage or to the ℞ assignment sequence module 580 to trigger a reassignment of a prescription to a new sequence of clerk, technician, and/or pharmacist.

In some embodiments (not shown), a prescription order may be subject to other kinds of exception handling, triggering a reassignment of a prescription order to a new clerk, technician, or pharmacist within the current stage, to any of the other stages. A reassigned task subject to an exception may join a queue of ordinary tasks or other tasks subject to an exception, and the queued tasks may be assigned to clerks, technicians, or pharmacists within their respective stages out of queue order, so as to optimize the overall performance (e.g., productivity, efficiency) of the prescription medication fulfillment system according to one or more performance metrics.

To add context to the prescription medication fulfillment system 500, consider a prescription medication fulfillment system with two pharmacists: Pharmacist A is new and inexperienced, whereas Pharmacist B has over ten years of experience and high ratings. The system also has two technicians. Technician A has a relatively high error rate or kick-back rate (i.e., pharmacists are more likely to kick scripts back to Technician A) as compared to Technician B, who has a relatively low error rate or kick-back rate. The system does not have any clerks.

A pairing strategy optimizing across an entire sequence may preferably pair some types of scripts with Technician A and Pharmacist B, because Pharmacist B can competently handle scripts mismanaged by Technician A. Other types of scripts may be preferably paired with Technician B and Pharmacist A, so that this newer pharmacist will be trained and gain experience from scripts that were already handled by a competent technician. A performance-based routing strategy might preferably route as many scripts as possible through Technician B and Pharmacist B. Even if those scripts are processed the fastest and with the lowest error rate, Technician B and Pharmacist B might get burned out, and Technician A and Pharmacist A get fewer opportunities to learn and gain experience.

Furthermore, not all scripts are equal. For example, a particularly challenging, unusual, expensive, or risky script may be preferably paired with Technician B and Pharmacist B, whereas a particularly routine, inexpensive, or low-risk script may be preferably paired with Technician A and Pharmacist A. Even if Technician A and Pharmacist A will take longer to handle the lower complexity script, it will leave Technician B and Pharmacist B available for a script of higher complexity, while also balancing utilization across all types of agents.

Performance of the system may be benchmarked or otherwise measured against whichever metrics should be optimized or whichever outcomes should be tracked. For example, handle time per agent, total handle time from script to ship, frequency of scripts getting kicked back or bounced back, types of medication, error rate, etc. may be measured and recorded. There may also be a constraint to reduce the number of outliers (e.g., scripts that take much longer than average to ship) and avoid inbound complaints from patients waiting longer than expected for their medication to ship.

FIG. 6 shows a multistage task assignment method 600 according to embodiments of the present disclosure. Multistage task assignment method 600 may begin at block 610. At block 610, one or more characteristics of a task in a multistage task assignment system may be determined. For example, in a prescription medication system, the level risk associated with a medication on a prescription, the cost of the medication, the unusualness of the prescription, etc. may be determined. Multistage task assignment method 600 may proceed to block 620. At block 620, based at least on the one or more characteristics of the task, a sequence of agents may be determined. For example, a sequence of agents may be determined to improve the performance of the multistage task assignment system, and may be determined by using a behavioral pairing strategy. The sequence of agents may be determined to optimize the multistage task assignment system to reduce an average total handle time for the task over multiple stages. Multistage task assignment method 600 may proceed to block 630. At block 630, the task may be paired with the sequence of agents. After paring the task with the sequence of agents, the multistage task assignment method 600 may end.

In some embodiments, the task assignment system and task assignment method may switch among multiple pairing models in real time based on the desired metric or combination of metrics to optimize and runtime conditions of the task assignment system. In some embodiments, the task assignment system may evaluate multiple models simultaneously and select the result giving the most optimal pairing for a single task assignment or sequence of task assignments. A pairing model may account for multiple goals, attributes, or variables and the interdependencies or interactions among the multiple goals, attributes, or variables.

In some embodiments, the task assignment system and task assignment method may account for one or more constraints on pairing, which in some cases may conflict with one another.

In some embodiments, the task assignment system and task assignment method may group tasks for batch processing by the same agent. For example, if two prescriptions both require assignment to the same physician for clarification, these tasks may be grouped into a single call or other assignment to the physician.

At this point it should be noted that behavioral pairing in a multistage task assignment system in accordance with the present disclosure as described above may involve the processing of input data and the generation of output data to some extent. This input data processing and output data generation may be implemented in hardware or software. For example, specific electronic components may be employed in a behavioral pairing module or similar or related circuitry for implementing the functions associated with behavioral pairing in a multistage task assignment system in accordance with the present disclosure as described above. Alternatively, one or more processors operating in accordance with instructions may implement the functions associated with behavioral pairing in a multi-stage task assignment system in accordance with the present disclosure as described above. If such is the case, it is within the scope of the present disclosure that such instructions may be stored on one or more non-transitory processor readable storage media (e.g., a magnetic disk or other storage medium), or transmitted to one or more processors via one or more signals embodied in one or more carrier waves.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of at least one particular implementation in at least one particular environment for at least one particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

The invention claimed is:

1. A method for pairing in a multistage task assignment system, the method comprising:
   receiving, by at least one computer processor communicatively coupled to and configured to operate in the multistage task assignment system, a request to complete a first task, wherein the first task is associated with a plurality of stages of performing a plurality of subtasks by a plurality of agents;
   determining, by the at least one computer processor, one or more characteristics for each stage of the plurality of stages; and
   determining, by the at least one computer processor, a first agent sequence for the first task based on the one or more characteristics for each stage of the plurality of stages, a first task assignment strategy, and a plurality of historical agent-task assignments, wherein determining the first agent sequence comprises determining a sequence of performing the plurality of sub-tasks for completing the first task and assigning an available agent to each of the plurality of sub-tasks, wherein the first agent sequence increases a first performance metric of the multistage task assignment system for the first task and decreases a second performance metric of the multistage task assignment system for at least one stage in the plurality of stages, wherein the first agent sequence for the first task is determined by establishing, in at least one switching component of the multistage task assignment system, at least one connection between one of the plurality of stages and an agent, wherein the method further comprises:
while the first task has at least one uncompleted stage, receiving, by the at least one computer processor, a second request to complete a second task, wherein the second task comprises a second plurality of stages;

determining, by the at least one computer processor, a second agent sequence, wherein the second agent sequence comprises assignments of available agents to uncompleted stages of the first task and at least one stage of the second plurality of stages of the second task, and wherein the second task is received by the multistage task assignment system after the first task is received, and the second agent sequence prioritizes at least one stage of the second plurality of stages of the second task over at least one uncompleted stage of the first task.

2. The method of claim 1, further comprising:
receiving, by the at least one computer processor, an instruction from an assigned agent of the first agent sequence;
determining, by the at least one computer processor, a second agent sequence for the first task, wherein the second agent sequence comprises assignments of available agents to uncompleted stages of the plurality of stages of the first task and an assignment of an available agent to at least one previously-completed stage of the plurality of stages.

3. The method of claim 1, further comprising providing, by the at least one computer processor, an outcome of a completed stage of the plurality of stages of the first task to an agent associated with an uncompleted stage of the plurality of stages, wherein the uncompleted stage is subsequent to the completed stage.

4. The method of claim 1, wherein determining the first agent sequence for the first task occurs over a period of time, wherein an available agent is selected for a subsequent stage of the plurality of stages after the multistage task assignment system receives a notification that a prior stage is completed or is about to be completed.

5. The method of claim 1, further comprising:
receiving, by the at least one computer processor, an instruction for the task assignment system to determine agent sequences based on a second task assignment strategy; and
determining, by the at least one computer processor, a second agent sequence for uncompleted stages of the plurality of stages of the first task.

6. A system for pairing in a multistage task assignment system, the system comprising:
at least one computer processor communicatively coupled to and configured to operate in the multistage task assignment system, wherein the at least one computer processor is further configured to:
receive a request to complete a first task, wherein the first task is associated with a plurality of stages of performing a plurality of sub-tasks by a plurality of agents;
determine one or more characteristics for each stage of the plurality of stages; and
determine a first agent sequence for the first task based on the one or more characteristics for each stage of the plurality of stages, a first task assignment strategy, and a plurality of historical agent-task assignments;

wherein determining the first agent sequence comprises determining a sequence of performing the plurality of sub-tasks for completing the first task and assigning an available agent to each of the plurality of sub-tasks, wherein the first agent sequence increases a first performance metric of the multistage task assignment system for the first task and decreases a second performance metric of the multistage task assignment system for at least one stage in the plurality of stages, and wherein the first agent sequence for the first task is determined by establishing, in at least one switching component of the multistage task assignment system, at least one connection between one of the plurality of stages and an agent, wherein the at least one computer processor is further configured to:
while the first task has at least one uncompleted stage, receive a second request to complete a second task, wherein the second task comprises a second plurality of stages;
determine a second agent sequence, wherein the second agent sequence comprises assignments of available agents to uncompleted stages of the first task and at least one stage of the second plurality of stages of the second task, and wherein the second task is received by the multistage task assignment system after the first task is received, and the second agent sequence prioritizes at least one stage of the second plurality of stages of the second task over at least one uncompleted stage of the first task.

7. The system of claim 6, wherein the at least one computer processor is further configured to:
receive an instruction from an assigned agent of the first agent sequence;
determine a second agent sequence for the first task, wherein the second agent sequence comprises assignments of available agents to uncompleted stages of the plurality of stages of the first task and an assignment of an available agent to at least one previously-completed stage of the plurality of stages.

8. The system of claim 6, wherein the at least one computer processor is further configured to provide an outcome of a completed stage of the plurality of stages of the first task to an agent associated with an uncompleted stage of the plurality of stages, wherein the uncompleted stage is subsequent to the completed stage.

9. The system of claim 6, wherein determining the first agent sequence for the first task occurs over a period of time, wherein an available agent is selected for a subsequent stage of the plurality of stages after the multistage task assignment system receives a notification that a prior stage is completed or is about to be completed.

10. The system of claim 6, wherein the at least one computer processor is further configured to:

receive an instruction for the task assignment system to determine agent sequences based on a second task assignment strategy; and determine a second agent sequence for uncompleted stages of the plurality of stages of the first task.

11. A multistage task assignment system comprising:

at least one computer processor for receiving, via a communication channel, a request to complete a first task, wherein the first task is associated with a plurality of stages of performing a plurality of sub-tasks by a plurality of agents; and one or more switches for routing an available agent to each of the plurality of sub-tasks, wherein a first agent sequence is determined for the first task based on one or more characteristics for each stage of the plurality of stages, a first task assignment strategy, and a plurality of historical agent-task assignments, determining the first agent sequence comprises determining a sequence of performing the plurality of sub-tasks for completing the first task and assigning an available agent to each of the plurality of sub-tasks, the first agent sequence increases a first performance metric of the multistage task assignment system for the first task and decreases a second performance metric of the multistage task assignment system for at least one stage in the plurality of stages, the first agent sequence for the first task is determined by establishing, in at least one switching component of the multistage task assignment system, at least one connection between one of the plurality of stages and an agent, the at least one computer processor is configured to:
while the first task has at least one uncompleted stage, receive a second request to complete a second task, wherein the second task comprises a second plurality of stages;

determine a second agent sequence, wherein the second agent sequence comprises assignments of available agents to uncompleted stages of the first task and at least one stage of the second plurality of stages of the second task, the second task is received by the multistage task assignment system after the first task is received, and wherein the second agent sequence prioritizes at least one stage of the second plurality of stages of the second task over at least one uncompleted stage of the first task.

12. The multistage task assignment system of claim 11, wherein the at least one computer processor is configured to:
receive an instruction from an assigned agent of the first agent sequence;
determine a second agent sequence for the first task, wherein the second agent sequence comprises assignments of available agents to uncompleted stages of the plurality of stages of the first task and an assignment of an available agent to at least one previously-completed stage of the plurality of stages.

13. The multistage task assignment system of claim 11, wherein the at least one computer processor is configured to provide an outcome of a completed stage of the plurality of stages of the first task to an agent associated with an uncompleted stage of the plurality of stages, wherein the uncompleted stage is subsequent to the completed stage.

14. The multistage task assignment system of claim 11, wherein determining the first agent sequence for the first task occurs over a period of time, wherein an available agent is selected for a subsequent stage of the plurality of stages after the multistage task assignment system receives a notification that a prior stage is completed or is about to be completed.

* * * * *